(12) United States Patent
Oka et al.

(10) Patent No.: US 10,302,558 B2
(45) Date of Patent: May 28, 2019

(54) GAS ANALYSIS SYSTEM AND BOILER

(71) Applicant: MITSUBISHI HEAVY INDUSTRIES, LTD., Tokyo (JP)

(72) Inventors: Hirotaka Oka, Tokyo (JP); Kenji Muta, Tokyo (JP); Tatsuyuki Nishimiya, Tokyo (JP); Kohei Kawazoe, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 15/560,744

(22) PCT Filed: Sep. 25, 2015

(86) PCT No.: PCT/JP2015/077026
§ 371 (c)(1),
(2) Date: Sep. 22, 2017

(87) PCT Pub. No.: WO2016/157573
PCT Pub. Date: Oct. 6, 2016

(65) Prior Publication Data
US 2018/0080869 A1    Mar. 22, 2018

(30) Foreign Application Priority Data

Mar. 31, 2015 (JP) .................................. 2015-071895

(51) Int. Cl.
*F27D 21/02* (2006.01)
*G01K 13/02* (2006.01)
(Continued)

(52) U.S. Cl.
CPC .............. *G01N 21/39* (2013.01); *F27D 21/02* (2013.01); *G01K 13/02* (2013.01); *G01N 21/61* (2013.01);
(Continued)

(58) Field of Classification Search
CPC ....... G01N 21/3504; G01N 2021/8578; G01N 21/85; G01N 33/225
See application file for complete search history.

(56) References Cited

U.S. PATENT DOCUMENTS 5,572,031 A * 11/1996 Cooper ................ G01D 3/0365
250/343
8,073,637 B2 * 12/2011 Cline ........................ G01J 3/02
702/28

(Continued)

FOREIGN PATENT DOCUMENTS

CN      101387607      3/2009
EP      1 703 206      9/2006
(Continued)

OTHER PUBLICATIONS

International Preliminary Report on Patentability dated May 9, 2017 in International (PCT) Application No. PCT/JP2015/077026, with English translation.
(Continued)

*Primary Examiner* — Shawn Decenzo
(74) *Attorney, Agent, or Firm* — Wenderoth, Lind & Ponack, L.L.P.

(57) ABSTRACT

A gas analysis system includes: a laser light source for emitting a laser light to be transmitted through an analysis target gas; a photodetector configured to receive the laser light transmitted through the analysis target gas, for outputting a signal corresponding to an emission intensity of the received laser light; a gas analysis apparatus for analyzing the analysis target gas on the basis of the signal outputted from the photodetector; a variable light attenuator disposed between the analysis target gas and the laser light source; a transmitted-light amount detector configured to evaluate a transmitted light amount of the laser light transmitted through the analysis target gas on the basis of the signal
(Continued)

outputted from the photodetector; and an attenuation amount controller configured to control an attenuation amount of the variable light attenuator on the basis of the transmitted light amount of the laser light evaluated by the transmitted-light amount detector.

13 Claims, 5 Drawing Sheets

(51) Int. Cl.
    *G01N 21/27* (2006.01)
    *G01N 21/39* (2006.01)
    *G01N 21/61* (2006.01)
    *G01N 33/00* (2006.01)

(52) U.S. Cl.
    CPC ..... *G01N 33/004* (2013.01); *G01K 2013/024* (2013.01); *G01N 21/274* (2013.01); *G01N 2021/399* (2013.01); *G01N 2201/0612* (2013.01); *Y02A 50/25* (2018.01)

(56) References Cited

U.S. PATENT DOCUMENTS

| | | | |
|---|---|---|---|
| 9,625,628 B2 * | 4/2017 | Hruska | ................ G01J 3/2803 |
| 9,863,887 B2 * | 1/2018 | Babichenko | ........... G01N 21/64 |
| 2006/0133714 A1 | 6/2006 | Sappey et al. | |
| 2006/0176486 A1 | 8/2006 | Ho | |
| 2009/0164138 A1 * | 6/2009 | Goto | ................. G01N 21/3504 702/24 |
| 2009/0229250 A1 * | 9/2009 | Yamakage | ......... G01N 15/0205 60/276 |
| 2009/0323068 A1 * | 12/2009 | Yamakage | ........... G01N 21/031 356/437 |
| 2010/0028819 A1 | 2/2010 | Knittel et al. | |
| 2014/0125967 A1 * | 5/2014 | Otera | .................... G01J 3/4338 356/51 |
| 2014/0176936 A1 * | 6/2014 | Van Mechelen | ... G01N 21/3504 356/73 |
| 2015/0293032 A1 * | 10/2015 | Babichenko | ........... G01N 21/64 356/70 |
| 2018/0202926 A1 * | 7/2018 | Black | ................. G01N 21/3504 |

FOREIGN PATENT DOCUMENTS

| | | |
|---|---|---|
| JP | 2001-74654 | 3/2001 |
| JP | 2003-513272 | 4/2003 |
| JP | 2006-227003 | 8/2006 |
| JP | 2006-522938 | 10/2006 |
| JP | 2006-337326 | 12/2006 |
| JP | 2008-51598 | 3/2008 |
| JP | 2008-164576 | 7/2008 |
| JP | 2009-222526 | 10/2009 |
| JP | 4467674 | 5/2010 |
| JP | 2010-519544 | 6/2010 |
| JP | 2010-185694 | 8/2010 |
| JP | 2010-217100 | 9/2010 |
| JP | 2010-237106 | 10/2010 |
| JP | 2012-225730 | 11/2012 |
| JP | 2013-117517 | 6/2013 |
| WO | 97/25609 | 7/1997 |
| WO | 01/33200 | 5/2001 |
| WO | 2005/111585 | 11/2005 |

OTHER PUBLICATIONS

International Search Report dated Dec. 1, 2015 in International (PCT) Application No. PCT/JP2015/077026.
Extended European Search Report (EESR) dated Aug. 6, 2018 in corresponding EP application No. 15887715.9.

* cited by examiner

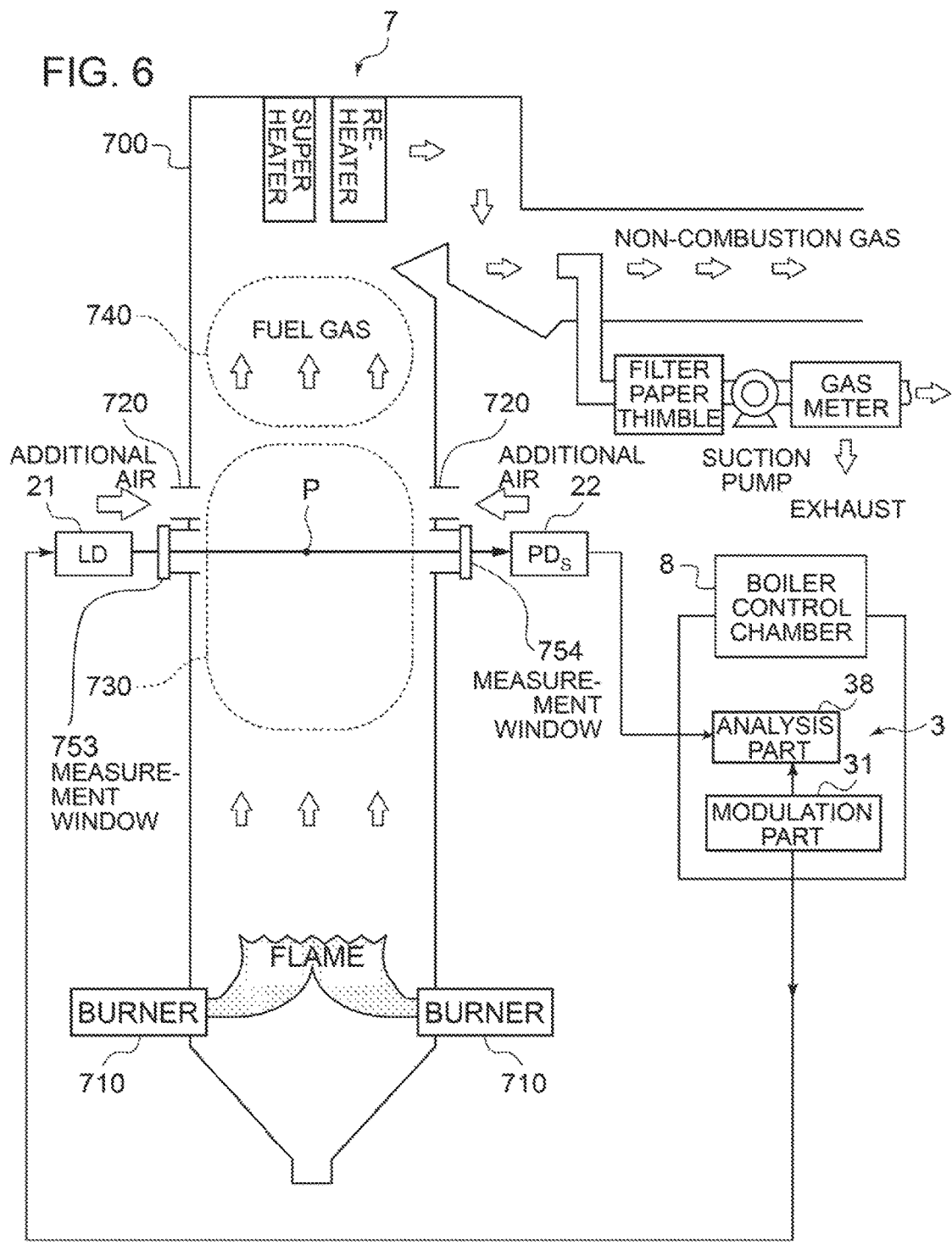

GAS ANALYSIS SYSTEM AND BOILER

TECHNICAL FIELD

The present disclosure relates to a gas analysis system and a boiler.

BACKGROUND ART

In recent years, a laser-type optical chemical-species sensor has been developed to deal with problems related to extraction measurement techniques. The laser-type measurement techniques can perform measurement "on site", and also has another advantage, which is a high-speed feedback suitable for a dynamic process control. The tunable diode laser absorption spectroscopy (TDLAS) is a particularly promising technique for measuring the composition and temperature of combustion gas and other combustion parameters. TDLAS is typically performed by a diode laser which operates in the near-infrared spectral region and the mid-infrared spectral region. Suitable lasers have been developed extensively to be used in the long-distance telecommunication industry, and are easily accessible for the TDLAS usage. Various TDLAS techniques have been developed, which are more or less suitable for detection and control of a combustion process. Commonly known techniques include the wavelength modulation spectroscopy, the frequency modulation spectroscopy, and the direct absorption spectroscopy. In each of the above techniques, light is conducted through a combustion process chamber, and is absorbed in a specific spectral band that uniquely corresponds to a gas that exists in the process chamber, or a combustion chamber, before being received by a detector. It is based on a pre-obtained relationship between the amount and the characteristics of laser light. The absorption spectrum received by the detector is used to obtain the amount of a gas chemical species to be analyzed, and a combustion parameter (e.g. temperature) related to the amount.

Furthermore, generally, TDLAS is performed by transmitting laser light that has passed through a target environment, and then detecting absorption of the laser light at a specific wavelength due to a target gas such as carbon monoxide and oxygen. The spectrum analysis on the detected light makes it possible to identify the type and amount of gas along a laser path. The laser absorption spectroscopy is contact-free, and thus is suitable for use in a severe environment, such as a combustion section in a coal combustion power plant, and a flammable or toxic environment where other types of probe cannot be used. While such an environment may cause extreme attenuation (typically, light loss over 90%), using laser light makes it possible to achieve a high luminance required to realize transmission which can be detected even under such attenuation. To bear the harsh condition of a target usage more suitably, laser light may be sent into a target environment through protected optical fiber (e.g. Patent Document 1).

Further, Patent Document 2 discloses a gas concentration measuring apparatus that uses the laser absorption spectroscopy, which includes a light source part capable of adjusting laser oscillation wavelengths to a plurality of absorption wavelengths inherent to a gas to be measured, a modulation part for applying modulation to the laser oscillation wavelengths emitted from the light source part and outputting a reference signal synchronized to the modulation, a light receiving part for receiving the laser light having passed through the target gas in a measuring region and outputting signals corresponding to the intensities of the received beams, a phase sensitive detection part for detecting the component synchronized to the modulation signal added to the laser light or the higher harmonic component from the signal of the light receiving part on the basis of the reference signal outputted from the modulation part and outputting the same, and an analyzing part for calculating the concentration of the target gas in the measuring region and the concentration of solid particles on the basis of the signal outputted from the phase sensitive detection part and the signal from the light receiving part.

Patent Document 3 discloses a laser type gas analyzer for receiving a laser light in a mid-infrared region including an optical absorption spectrum of a measurement target gas, and calculating gas concentration from an amount of change of a signal component affected by optical absorption by the measurement target gas. The laser type gas analyzer includes: a near-infrared laser emission part for emitting a laser light of a near-infrared region including an optical absorption spectrum of water being present in an inside of a flue without including the optical absorption spectrum of the measurement target gas; an optical system such as a lens for irradiating the inside of the flue with a near-infrared laser light; a lens and a near-infrared photodetector for receiving the near-infrared laser light and outputting it as an electric signal; a water concentration calculation part for extracting a signal component affected by optical absorption by water being present in the inside of the flue from the electric signal and calculating water concentration from the amount of change therein; and a gas concentration correction part for correcting a concentration measurement value of the measurement target gas calculated by using mid-infrared laser light on the basis of the water concentration.

CITATION LIST

Patent Literature

Patent Document 1: JP2006-522938A (translation of a PCT application)
Patent Document 2: JP44676748
Patent Document 3: JP2013-117517A

SUMMARY

Problems to be Solved

In the laser absorption spectroscopy disclosed in Patent Document 1, if a combustion gas to be analyzed contains a high concentration of soot and dust, it leads to not only attenuation of the laser light by the analysis target gas but also to remarkable attenuation of the laser intensity (typically, light loss over 99%) from an influence of diffusion or the like due to soot and dust, which makes it difficult to analyze the analysis target gas accurately.

Further, also with the gas concentration measuring apparatus disclosed in Patent Document 2, if a combustion gas to be analyzed contains a high concentration of soot and dust, it leads to not only attenuation of the laser light by the analysis target gas but also to remarkable attenuation of the laser intensity (typically, light loss over 99%) from an influence of diffusion or the like due to soot and dust, which makes it difficult to analyze the analysis target gas accurately.

Furthermore, if a laser-type gas analysis meter is designed to have a light-receiving sensitiveness suited for measurement in an environment where the laser intensity is attenuated remarkably (typically, light loss over 99%) from an influence of diffusion or the like due to soot and dust, it is difficult to analyze an analysis target gas accurately when the concentration of soot and dust becomes low and the emission intensity of laser light gets high, for the light-receiving element (photodetector) becomes saturated.

In view of the above, an object of at least one embodiment of the present invention is to provide a gas analysis system and a boiler including the same, whereby it is possible to analyze an analysis target gas even when the analysis target gas contains a high concentration of soot and dust, and whereby it is also possible to analyze an analysis target gas accurately even when the concentration of soot and dust contained in the analysis target gas becomes low.

Solution to the Problems (1) A gas analysis system according to at least one embodiment of the present invention comprises: a laser light source for emitting a laser light to be transmitted through an analysis target gas; a photodetector configured to receive the laser light transmitted through the analysis target gas, for outputting a signal corresponding to an emission intensity of the received laser light; a gas analysis apparatus for analyzing the analysis target gas on the basis of the signal outputted from the photodetector; a variable light attenuator disposed between the analysis target gas and the laser light source; a transmitted-light amount detector configured to evaluate a transmitted light amount of the laser light transmitted through the analysis target gas on the basis of the signal outputted from the photodetector; and an attenuation amount controller configured to control an attenuation amount of the variable light attenuator on the basis of the transmitted light amount of the laser light evaluated by the transmitted-light amount detector.

With this configuration (1), provided is the attenuation amount controller which controls the attenuation amount of the variable light attenuator on the basis of the transmitted light amount of laser light evaluated by the transmitted-light amount detector, and thus it is possible to analyze the analysis target gas even when the concentration of soot and dust contained in the analysis target gas is high, and also it is possible to analyze the analysis target gas accurately even when the concentration of soot and dust contained in the analysis target gas becomes low. Specifically, with the photodetector having a high sensitiveness, it is possible to analyze the analysis target gas even when the concentration of soot and dust is high. Furthermore, even when the concentration of soot and dust contained in the analysis target gas becomes low, it is possible to analyze the analysis target gas accurately with the photodetector still having a high sensitiveness by increasing the attenuation amount of the variable light attenuator.

(2) In some embodiments, in the above configuration (1), the photodetector is configured to output an output voltage in proportion to the emission intensity of the received laser light as the signal, and the transmitted-light amount detector is configured to evaluate the transmitted light amount of the laser light transmitted through the analysis target gas on the basis of the output voltage outputted from the photodetector.

With the above configuration (2), while the photodetector outputs as a signal the output voltage which is in proportion to the emission intensity of the received laser light, the transmitted-light amount detector evaluates the transmitted light amount of laser light having transmitted through the analysis target gas on the basis of the output voltage outputted from the photodetector, and thereby it is possible to simplify evaluation of the transmitted light amount of laser light.

(3) In some embodiments, in the above configuration (1) or (2), the attenuation amount controller is configured to increase the attenuation amount if an intensity of the laser light evaluated by the transmitted-light amount detector is greater than a threshold, and to reduce the attenuation amount if the intensity of the laser light is not greater than the threshold.

With the above configuration (3), the attenuation amount is increased if the intensity of laser light evaluated by the transmitted-light amount detector is greater than a threshold, and the attenuation amount is reduced if the intensity of the laser light is not greater than the threshold, which makes it possible to maintain the emission intensity of laser light having transmitted through the analysis target gas appropriately. Accordingly, it is possible to analyze the analysis target gas even when the concentration of soot and dust contained in the analysis target gas is high, and also it is possible to analyze the analysis target gas accurately even when the concentration of soot and dust contained in the analysis target gas becomes low.

(4) In some embodiments, in the above configuration (3), the threshold is set to a value which is at least 80% of a maximum output value of the photodetector.

With the above configuration (4), the threshold is set to a value not less than 80% of the maximum output value of the photodetector, and thus the attenuation amount is reduced if the intensity of laser light is less than 80% of the maximum output value of the photodetector. Accordingly, light of at least 80% of the maximum output value enters the photodetector, and thus it is possible to maintain a high detection accuracy.

(5) In some embodiments, in any one of the above configurations (1) to (4), the laser light source is disposed so that the laser light transmits through a combustion gas which serves as the analysis target gas, at an observation point disposed inside a furnace of a boiler.

With the above configuration (5), laser light emitted from the laser light source transmits through combustion gas, which is an analysis target gas, at the observation point disposed inside the furnace of the boiler, and thereby it is possible to analyze combustion gas disposed at the observation point disposed inside the furnace. Specifically, by increasing the sensitivity of the photodetector, it is possible to analyze combustion gas even when a high concentration of soot and dust is contained in the combustion gas at the observation point. Furthermore, even when the concentration of soot and dust contained in the combustion gas becomes low, it is possible to analyze the combustion gas with the photodetector still having a high sensitiveness, by increasing the attenuation amount of the variable light attenuator.

(6) In some embodiments, in the above configuration (5), the observation point is disposed between a burner of the boiler and an additional air supplying part, inside the furnace.

With the above configuration (6), laser light emitted from the laser light source transmits through combustion gas, which is the analysis target gas, at the observation point disposed between the burner and the additional air supplying part, and thereby it is possible to analyze combustion gas in the reduction combustion region disposed between the burner and the additional air supplying part.

(7) In some embodiments, in the above configuration (5) or (6), the gas analysis apparatus is configured to analyze an oxygen concentration, a carbon monoxide concentration, and a gas temperature of the combustion gas serving as the analysis target gas, at the observation point.

With the above configuration (7), the gas analysis apparatus analyzes the oxygen concentration, the carbon monoxide concentration, and the gas temperature of combustion gas, which is an analysis target gas, at the observation point, and thereby it is possible to determine the operational state of the boiler.

(8) In some embodiments, in any one of the above configurations (1) to (7), the gas analysis system further comprises: a light distributor, disposed between the laser light source and the variable light attenuator, for distributing a part of the laser light emitted from the laser light source; a reference cell which contains a predetermined amount of the analysis target gas and through which the part of the laser light distributed by the light distributor transmits; and a standard photo detector configured to receive the part of the laser light transmitted through the reference cell, for outputting a standard signal corresponding to an emission intensity of the part of the received laser light. The gas analysis apparatus is configured to calibrate an analysis result of the analysis target gas on the basis of the standard signal outputted by the standard photodetector.

With the above configuration (8), the analysis result of the analysis target gas is calibrated on the basis of the standard signal outputted by the standard photodetector, and then the analysis result of the analysis target gas analyzed on the basis of the emission intensity of the laser light attenuated by the variable light attenuator can be compared with. Further, the light distributor is disposed between the laser light source and the variable light attenuator, which is upstream of the variable light attenuator, and thus laser light before being attenuated by the variable light attenuator is distributed to the reference cell. Accordingly, the reference cell is analyzed by laser light having an appropriate emission intensity, and thus the analysis target gas is analyzed by laser light adjusted to an emission intensity suitable for the concentration of soot and dust contained in the analysis target gas. Accordingly, the reference cell can be analyzed with laser light having a suitable emission intensity which is higher than the emission intensity of laser light adjusted to an emission intensity suitable for the concentration of soot and dust.

(9) In some embodiments, in any one of the above configurations (1) to (8), the gas analysis system further comprises a measurement cell, disposed between the variable light attenuator and the photo detector, for extracting the analysis target gas.

With the above configuration (9), it is possible to analyze the analysis target gas even when the analysis target gas extracted by the measurement cell contains a high concentration of soot and dust, and also it is possible to analyze the analysis target gas accurately even when the concentration of soot and dust contained in the analysis target gas becomes low.

(10) In some embodiments, in any one of the above configurations (1) to (8), the gas analysis system further comprises: an insertion measurement probe to be inserted into a measurement target site where the analysis target gas exists; a first optical fiber inserted through the insertion measurement probe, for guiding the laser light from the variable light attenuator to the measurement target site; and a second optical fiber inserted through the insertion measurement probe, for guiding the laser light from the measurement target site to the photo detector.

With the above configuration (10), the insertion measurement probe can be inserted into the measurement target site where the analysis target gas exists. Accordingly, it is possible to analyze the analysis target gas which exists in the target measurement site into which the insertion measurement probe can be easily inserted.

(11) In some embodiments, in the above configuration (10), the insertion measurement probe has a measurement part disposed in a light path between an output surface of the first optical fiber from which the laser light is emitted and an input surface of the second optical fiber into which the laser light enters, and the analysis target gas exists at the measurement part.

With the above configuration (11), the analysis target gas exists at the measurement part disposed in the light path between the output surface of the first optical fiber from which the laser light is emitted and the input surface of the second optical fiber into which the laser light enters, and thus it is possible to analyze the analysis target gas reliably. Further, it is possible to reduce the length of the light path, and thus it is possible to obtain data in a local range through which the laser light transmits, even when the concentration of soot and dust is high and the analysis target gas cannot be analyzed as a whole.

(12) In some embodiments, in any one of the above configurations (1) to (11), the gas analysis system further comprises a low-pass filter for removing a noise component, disposed between the photo detector and the transmitted-light amount detector.

With the above configuration (12), the low-pass filter removes a noise component, and thus it is possible to analyze the analysis target gas accurately.

(13) A boiler according to at least some embodiments of the present invention comprises: a furnace; a burner for combusting fuel in the furnace; and the gas analysis system according to any one of the above (1) to (12), configured to analyze a combustion gas in the furnace at a downstream side of the burner.

With the above configuration (13), with the gas analysis system according to any one of the above (1) to (12) for analyzing combustion gas in the furnace at the downstream side of the burner, it is possible to analyze combustion gas with high accuracy even if the concentration of soot and dust changes considerably in response to a change in the operational condition of the boiler (e.g. a change in the type of fuel, increase or decrease in the efficiency).

(14) In some embodiments, in the above configuration (13), the boiler further comprises an additional air supplying part for supplying an additional combustion air into the furnace, at the downstream side of the burner. The gas analysis system is configured to analyze the combustion gas at a position downstream of the burner and upstream of the additional air supplying part, inside the furnace.

With the boiler having the above configuration (14), a reduction combustion region is formed on the downstream side of the burner and the upstream side of the additional air supplying part. The composition of combustion gas in the reduction combustion region is an important piece of information for appropriate operation control for the boiler. However, the concentration of soot and dust in the reduction combustion region is high, and thus it is not easy to analyze combustion gas in the reduction combustion region.

In this regard, with the above configuration (14), it is possible to perform an accurate analysis on combustion gas in the reduction combustion region where the concentration of soot and dust is high, and thereby to perform an appropriate operation control on the boiler.

Advantageous Effects

According to at least one embodiment of the present invention, it is possible to provide a gas analysis system whereby it is possible to analyze an analysis target gas even when the analysis target gas contains a high concentration of soot and dust, and whereby it is also possible to analyze an analysis target gas accurately even when the concentration of soot and dust contained in the analysis target gas becomes low.

BRIEF DESCRIPTION OF DRAWINGS

FIG. 6 is a conceptual diagram of a boiler provided with a gas analysis system according to an embodiment.

DETAILED DESCRIPTION

Embodiments of the present invention will now be described in detail with reference to the accompanying drawings. It is intended, however, that unless particularly specified, dimensions, materials, shapes, relative positions and the like of components described in the embodiments shall be interpreted as illustrative only and not intended to limit the scope of the present invention.

For instance, an expression of relative or absolute arrangement such as "in a direction", "along a direction", "parallel", "orthogonal", "centered", "concentric" and "coaxial" shall not be construed as indicating only the arrangement in a strict literal sense, but also includes a state where the arrangement is relatively displaced by a tolerance, or by an angle or a distance whereby it is possible to achieve the same function.

Further, for instance, an expression of a shape such as a rectangular shape or a cylindrical shape shall not be construed as only the geometrically strict shape, but also includes a shape with unevenness or chamfered corners within the range in which the same effect can be achieved.

On the other hand, an expression such as "comprise", "include", "have", "contain" and "constitute" are not intended to be exclusive of other components.

Figure 1:
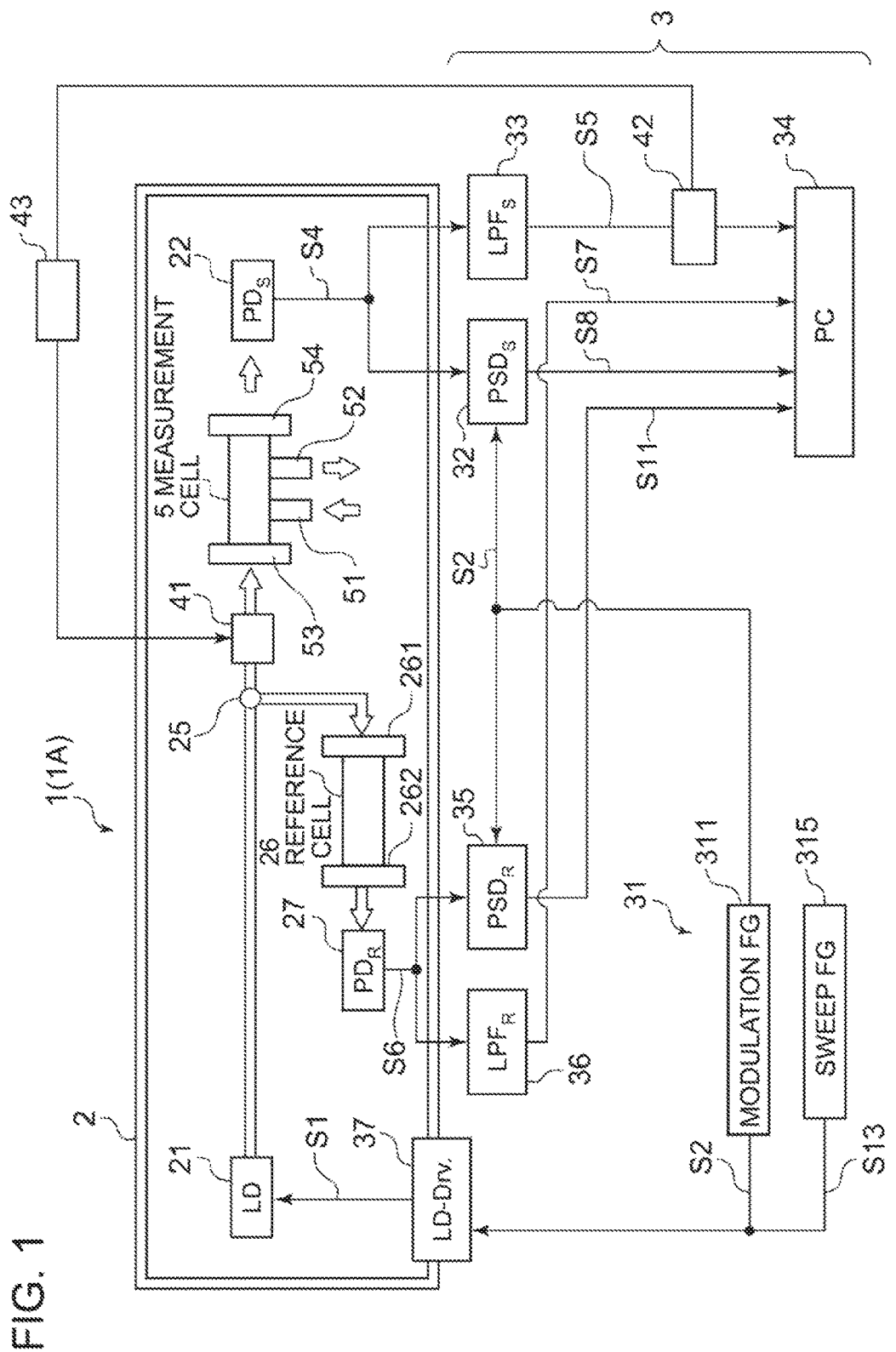
FIG. 1 is a schematic configuration diagram of a gas analysis system according to an embodiment of the present invention.
Figure 2:
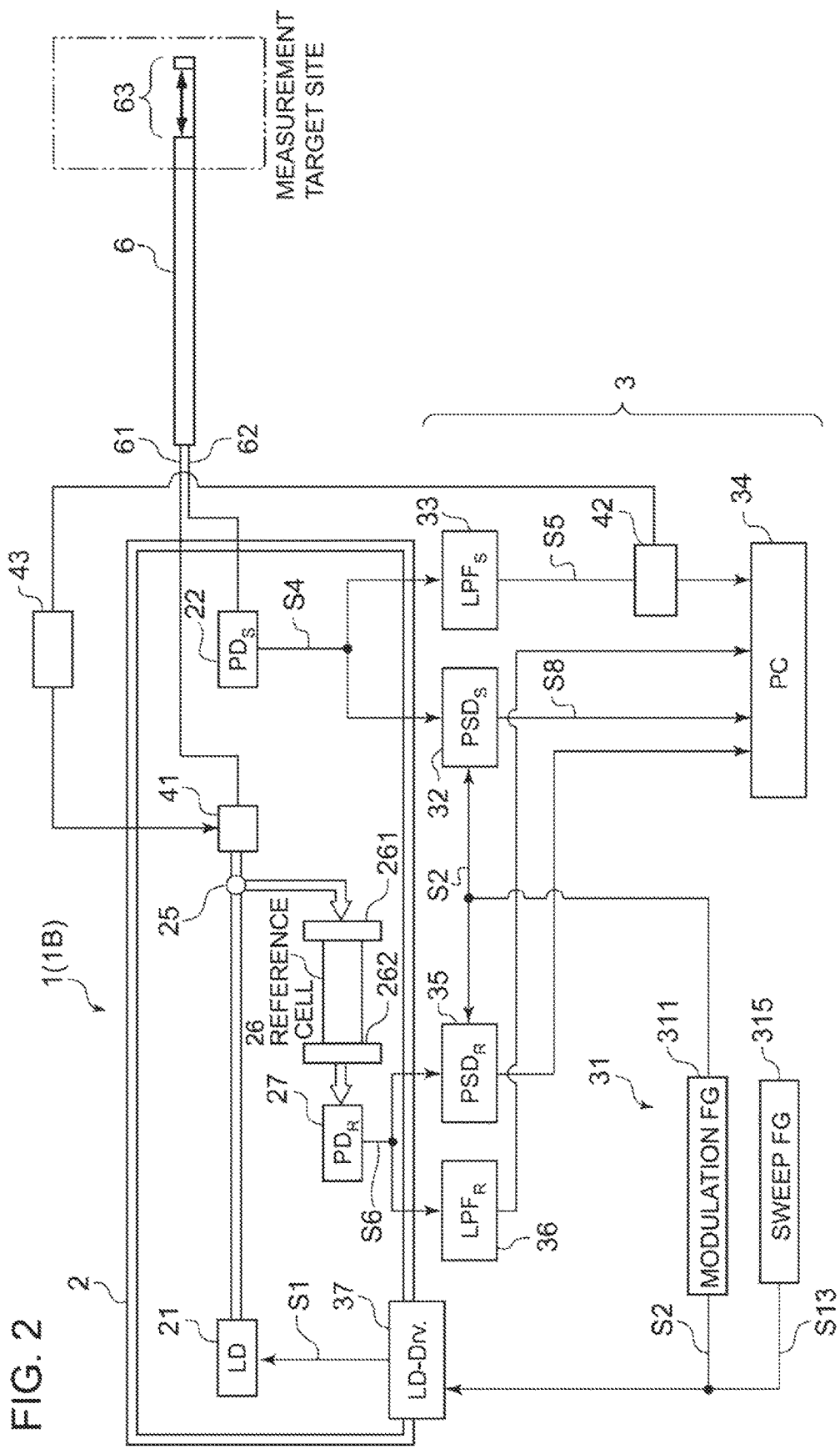
FIG. 2 is a schematic configuration diagram of a gas analysis system according to an embodiment.
Figure 3:
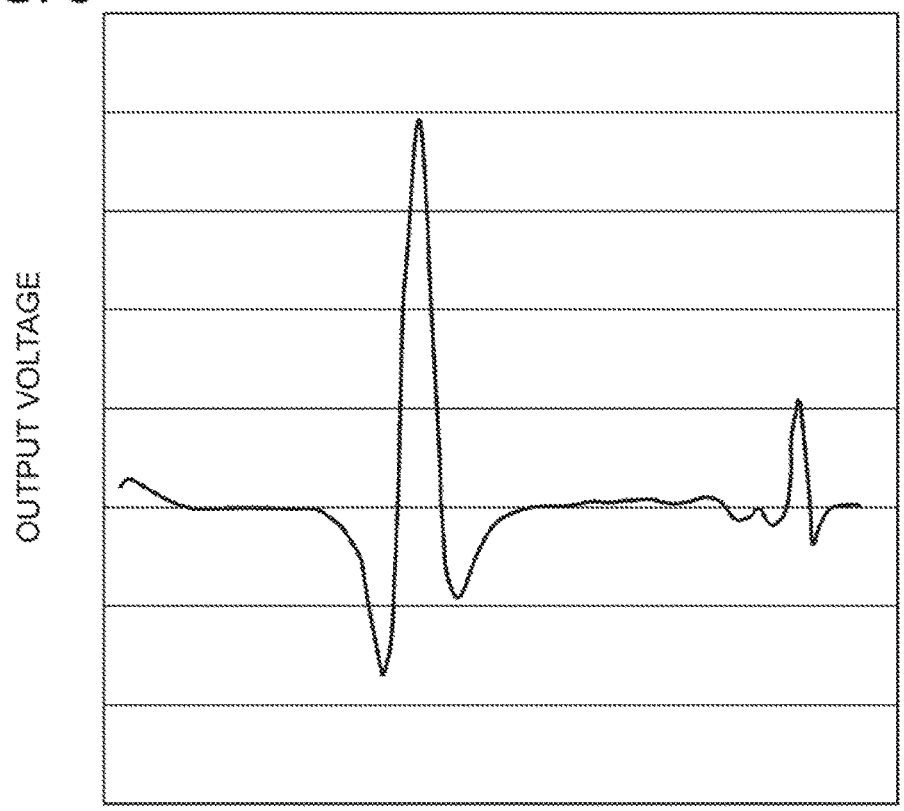
FIG. 3 is a diagram of a signal obtained by the phase sensitive detector depicted in FIGS. 1 and 2.
Figure 4:
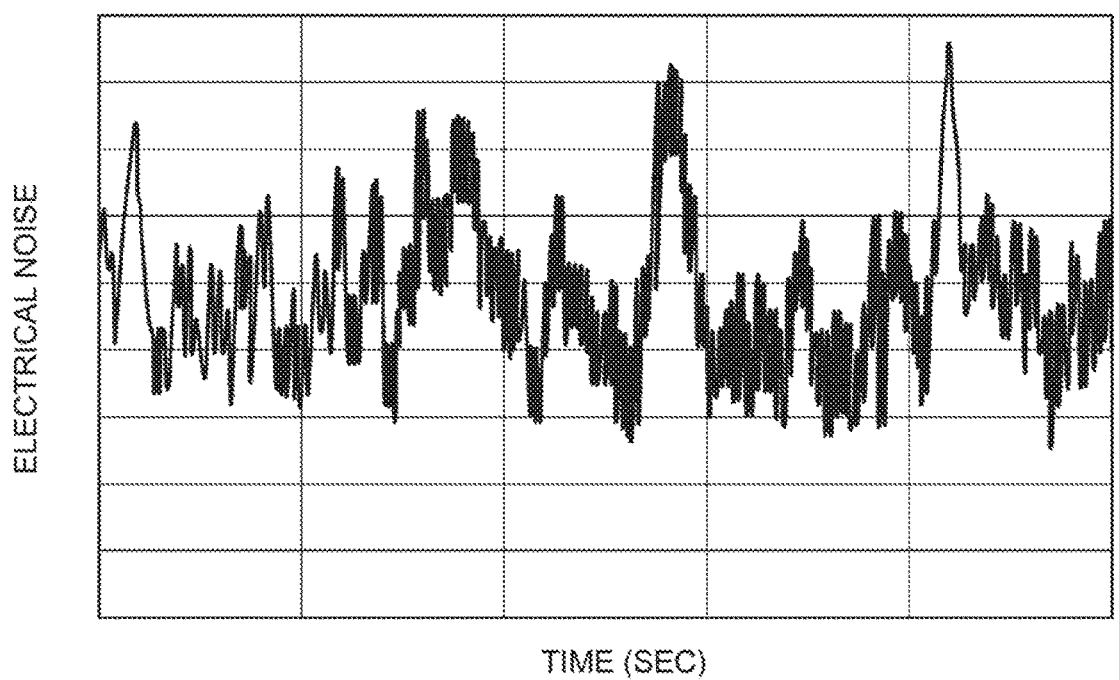
FIG. 4 is a diagram showing a noise level obtained by the phase sensitive detector depicted in FIGS. 1 and 2.

FIG. 1 is a schematic configuration diagram of a gas analysis system 1 (1A) according to an embodiment of the present invention. FIG. 2 is a schematic configuration diagram of a gas analysis system (1B) according to another embodiment of the present invention. FIG. 3 is a diagram of a signal obtained by the phase sensitive detector 32 depicted in FIGS. 1 and 2. FIG. 4 is a diagram showing a signal (noise level) obtained in a non-input state by the phase sensitive detector 32 depicted in FIGS. 1 and 2.

As depicted in FIGS. 1 and 2, the gas analysis system 1 (1A, 1B) according to some embodiments of the present invention includes a laser light source 21, a photodetector 22, a gas analysis apparatus 3, a variable light attenuator 41, a transmitted-light amount detector 42, and an attenuation amount controller 43.

In the embodiment depicted in FIGS. 1 and 2, the laser light source 21, the photodetector 22, and the variable light attenuator 41 are housed in a vessel 2, for instance, which is purged with inert gas (e.g. nitrogen gas).

The laser light source 21 emits laser light to be transmitted through an analysis target gas.

In the embodiments depicted in FIGS. 1 and 2, the laser light source 21 comprises a laser diode (LD). However, the laser light source 21 is not limited to this and may comprise a quantum-cascade laser, for instance.

The photodetector 22 outputs signals corresponding to the emission intensity of received laser light, and receives laser light having transmitted through an analysis target gas.

In the embodiment depicted in FIGS. 1 and 2, the photodetector 22 comprises a photo diode ($PD_S$). The photo diode ($PD_S$) receives laser light having transmitted through an analysis target gas, and outputs a signal corresponding to the intensity of the laser light.

In the embodiment depicted in FIGS. 1 and 2, the photodetector 22 has a high sensitivity to output a signal corresponding to the intensity, and is capable of detecting laser light having a low emission intensity by adjusting the gain.

The gas analysis apparatus 3 is for analyzing an analysis target gas on the basis of a signal outputted from the photodetector 22.

In the embodiments depicted in FIGS. 1 and 2, the gas analysis apparatus 3 obtains an absorption spectrum of infrared light having a specific wavelength by an analysis target gas from an emission intensity signal of laser light obtained by the photodetector 22, and calculates gas concentration from the absorption spectrum.

Further, in the embodiments illustrated in FIGS. 1 and 2, the gas analysis apparatus 3 includes a modulation part 31, a phase sensitive detector 32, a DC component detector 33, and a personal computer (PC) 34.

As depicted in FIGS. 1 and 2, the modulation part 31 applies modulation of different frequencies to laser emission wavelengths emitted from the laser light source 21, and outputs a reference signal synchronized with each modulation. The modulation part 31 includes a first function generator (modulation component generator, or modulation FG) 311. The first function generator 311 outputs a modulation signal S2 for applying modulation to the laser emission wavelength of the laser light source 21 to a light source driver 37, and outputs a reference signal S2 synchronized with the signal to the phase sensitive detector 32.

As depicted in FIG. 3, the output signal from the phase sensitive detector 32 has an apparent peak, and the level of the output signal (peak height) is in proportion to the absorption amount of laser light, whereby it is possible to obtain the gas concentration of the analysis target gas. Furthermore, as depicted in FIG. 4, the signal level obtained in a laser-light input state is clearly different from the signal level (noise level) that can be obtained while the phase sensitive detector 32 is in a non-input state, and thus the signal level obtained in a laser-light input state is sufficiently distinguishable from the signal at the noise level. For instance, the level of the output signal from the phase sensitive detector 32 and the signal level obtained in a non-input state have an S/N ratio of 10 or more, and the signal level obtained in a laser-light input state is sufficiently distinguishable from the signal at the noise level.

As illustrated in FIGS. 1 and 2, the phase sensitive detector 32 includes a lock-in amplifier (PSDs) which detects the absorption amount of laser light by oxygen molecules contained in the analysis target gas on the basis of the reference signal S2 from the first function generator 311 and the light-receiving signal S4 from the photodetector 22.

As shown in FIGS. 1 and 2, the DC component detector 33 includes a low-pass filter (LPFs) which detects a DC component (which corresponds to the transmission factor of laser light) in the light receiving signal S4 of the photodetector 22. The low-pass filter (LPFs) outputs a DC component signal S5, obtained by excluding an AC component such as a modulation component and a noise component from the light-receiving signal S4, to the personal computer (PC) 34 that serves as an analysis part.

The personal computer (PC) 34 includes a computation part (not depicted) which calculates an oxygen concentration and a solid particle concentration contained in the analysis target gas on the basis of signals from the phase sensitive detector 32 and the DC component detector 33, and a display device (not depicted) which displays each concentration value calculated by the computation part on a screen in numerical terms or as a graph.

In the embodiments depicted in FIGS. 1 and 2, the concentration of gas can be obtained by dividing the signal obtained by the phase sensitive detector 32 by the signal obtained by the DC component detector 33.

Further, in the embodiments depicted in FIGS. 1 and 2, the gas analysis apparatus 3 further includes a second function generator (wavelength sweep function generator, or sweep FG) 315 which outputs a signal S13 for slowly sweeping the laser emission wavelength for the purpose of measuring an oxygen absorption spectrum.

The variable light attenuator 41 is disposed between the analysis target gas and the laser light source 21.

A transmitted-light amount detector 42 is for evaluating the transmitted light amount of laser light having transmitted through the analysis target gas, and evaluates the transmitted light amount of the laser light on the basis of a signal outputted from the photodetector 22.

The attenuation amount controller 43 is for controlling the attenuation amount of the variable light attenuator 41, and controls the attenuation amount of the variable light attenuator 41 on the basis of the transmitted light amount of the laser light evaluated by the transmitted-light amount detector 42.

For instance, with the above configuration, assuming that the output limit of the photodetector 22 is 10V, if there is an input of 10 mW when the gain of the photodetector 22 is $8.0 \times 10^2$ V/W, the photodetector 22 outputs 8.0V. Accordingly, it is possible to measure an input of 10 mW.

However, if laser light to be measured is 0.1 mW, the gain needs to be multiplied by a hundred times ($8.0 \times 10$ V/W) to output 8.0V to ensure the S/N. If laser light of 10 mW is input in this case, the photodetector outputs 800V in a linear output but the output limit of the photodetector 22 is limited to 10V, and thus the output of the photodetector 22 is saturated, which leads to failure of detection of a change in the detection signal accompanying modulation, making the measurement impossible.

The above configuration prevents such failure by adjusting the attenuation amount of the variable light attenuator 41.

While one may consider adjusting the gain of the photodetector 22, adjusting the gain would change the characteristics of the photodetector 22 and affect the time constant of detection, which may require another standard curve and calibration. Thus, changing the gain during measurement should be avoided (the gain should be constant).

Further, while one may consider changing the output amount of the laser light source 21, the laser light source 21 has a characteristic that changing a current value leads to displacement of the wavelength of the laser light. Thus, in measurement such as gas analysis where the wavelength is specifically targeted, the output amount of the laser light source 21 should not be changed during measurement.

In this regard, with the variable light attenuator 41 provided between the analysis target gas and the laser light source 21 and controlled suitably, it is possible to analyze the analysis target gas whether the amount of soot and dust is great or small, without changing the gain of the photodetector 22 or the output of the laser light source 21.

With this configuration, provided is the attenuation amount controller 43 which controls the attenuation amount of the variable light attenuator 41 on the basis of the transmitted light amount of laser light evaluated by the transmitted-light amount detector 42, and thus it is possible to analyze the analysis target gas even when the concentration of soot and dust contained in the analysis target gas is high, and also it is possible to analyze the analysis target gas even when the concentration of soot and dust contained in the analysis target gas becomes low. Specifically, by increasing the sensitivity of the photodetector 22, it is possible to analyze the analysis target gas even when the concentration of soot and dust is high. Furthermore, even when the concentration of soot and dust contained in the analysis target gas becomes low, it is possible to analyze the analysis target gas accurately with the photodetector 22 still having a high sensitiveness, by increasing the attenuation amount of the variable light attenuator 41.

Thus, it is possible to analyze the analysis target gas with high accuracy even if the concentration of soot and dust contained in the analysis target gas changes considerably (e.g. in a range of 0 to 15 g/m$^3$).

As depicted in FIGS. 1 and 2, in some embodiments, the photodetector 22 outputs as a signal the output voltage which is in proportion to the emission intensity of the received laser light, and the transmitted-light amount detector 42 evaluates the transmitted light amount of laser light having transmitted through the analysis target gas on the basis of the output voltage outputted from the photodetector 22.

In the embodiments illustrated in FIGS. 1 and 2, as described above, the photodetector 22 comprises a photo diode (PD$_S$) which outputs as a signal the output voltage which is in proportion to the emission intensity of the received laser light, and the transmitted-light amount detector 42 evaluates the transmitted light amount of laser light having transmitted through the analysis target gas on the basis of the output voltage outputted from the photo diode (PD$_S$).

With the above configuration, while the photodetector 22 outputs as a signal the output voltage which is in proportion to the emission intensity of the received laser light, the transmitted-light amount detector 42 evaluates the transmitted light amount of laser light having transmitted through the analysis target gas on the basis of the output voltage outputted from the photodetector 22, and thereby it is possible to simplify evaluation of the transmitted light amount of laser light.

As depicted in FIGS. 1 and 2, in some embodiments, a low-pass filter (LPFs) for removing a noise component is further provided between the photodetector 22 and the transmitted-light amount detector 42.

With the above configuration, the low-pass filter (LPFs) removes a noise component, and thus it is possible to evaluate the transmitted light amount of laser light appropriately with the transmitted-light amount detector 42 and to analyze the analysis target gas accurately.

As depicted in FIG. 1, in some embodiments, a measurement cell 5 for extracting the analysis target gas is disposed between the variable light attenuator 41 and the photodetector 22.

An input window 53 is disposed on an end of the measurement cell 5, and an output window 54 is disposed on the other end of the measurement cell 5.

The light distributor 25 and the variable light attenuator 41 described above are disposed in front of the input window 53, and the laser light source 21 is disposed in front of the light distributor 25 and the variable light attenuator 41 (herein, "front" means the upstream side with respect to the emitting direction of laser light). The laser light emitted from the laser light source 21 passes through the light distributor 25 to become a partially transmitted light, and is attenuated by the variable light attenuator 41, before being input to the measurement cell 5 via the input window 53. The emitting operation of the laser light source 21 is controlled by the control signal S1 from the light source driver 37. The light source driver 37 includes a control circuit for matching the emission wavelength of the laser light source 21 with one of the absorption wavelengths specific to oxygen molecules ($O_2$).

The above described photodetector 22 is disposed behind the output window 54. The photodetector 22 receives laser light having passed through the measurement cell 5, and outputs a light receiving signal S4 corresponding to the intensity of the laser light to the phase sensitive detector 32 and the DC component detector 33. Herein, "behind" means the downstream side with respect to the emitting direction of the laser light.

With this configuration, it is possible to analyze the analysis target gas even when the analysis target gas extracted by the measurement cell 5 contains a high concentration of soot and dust, and it is also possible to analyze the analysis target gas accurately even when the concentration of soot and dust contained in the analysis target gas becomes low.

As depicted in FIGS. 1 and 2, in some embodiments, the light distributor 25, the reference cell 26, and a photodetector (standard photodetector) 27 are further provided.

The light distributor 25 is for distributing a part of laser light emitted from the laser light source 21, and is disposed between the laser light source 21 and the variable light attenuator 41.

In the embodiments depicted in FIGS. 1 and 2, the light distributor 25 comprises a beam splitter (not depicted), for instance. A mirror (not depicted) is disposed in the vicinity of the beam splitter, and a part of laser light divided by the beam splitter is reflected by the mirror to be input into the reference cell 26.

The reference cell 26 contains a predetermined amount of reference gas, and is configured to let through a part of laser light distributed by the light distributor 25.

In the embodiments depicted in FIGS. 1 and 2, a part of laser light enters the reference cell 26 through a window 261, and after passing through the reference cell 26, exits from the reference cell 26 through a window 262. A part of laser light that has passed through the reference cell 26 is received by the photodetector 27.

The photodetector 27 outputs standard signals corresponding to the emission intensity of received laser light, and receives a part of laser light having transmitted through the reference cell.

In the embodiments depicted in FIGS. 1 and 2, the photodetector 27 comprises a photo diode ($PD_R$). The photo diode ($PD_R$) receives laser light having transmitted through the analysis target gas, and outputs a signal corresponding to the intensity of the laser light.

In the embodiments illustrated in FIGS. 1 and 2, the gas analysis apparatus 3 further includes a phase sensitive detector 35 and a DC component detector 36.

In the embodiments depicted in FIGS. 1 and 2, the first function generator (modulation component generator (FG)) 311 outputs, to the phase sensitive detector 35, a reference signal S2 synchronized with the modulation signal S2 for applying modulation to the laser emission wavelength of the laser light source 21.

As depicted in FIGS. 1 and 2, the phase sensitive detector 35 includes a lock-in amplifier ($PSD_R$) which detects the absorption amount of laser light by oxygen molecules contained in the reference gas from the reference signal S2 from the first function generator 311 and the light-receiving signal S6 from the photodetector 27. The lock-in amplifier ($PSD_R$) outputs, to the personal computer (PC) 34, a signal S11 which represents the intensity of a component that synchronizes with the second harmonic of the reference signal (first modulation signal) from the AC component of the light-receiving signal S6.

As shown in FIGS. 1 and 2, the DC component detector 36 includes a low-pass filter ($LPF_R$) which detects a DC component (which corresponds to the transmission factor of laser light) from the light receiving signal S6 of the photodetector 27. The low-pass filter ($LPF_R$) outputs a IX component signal S7, obtained by excluding an AC components such as a modulation component and a noise component from the light-receiving signal S6, to a personal computer (PC) 34 that serves as an analysis part.

The personal computer (PC) calibrates the analysis result of the analysis target gas on the basis of the signal outputted by the photodetector 27.

With the above configuration, the analysis result of the analysis target gas is calibrated on the basis of the standard signal outputted by the photodetector 27, and thus the analysis result of the analysis target gas analyzed on the basis of the emission intensity of the laser light attenuated by the variable light attenuator 41 can be compared with. Further, the light distributor 25 is disposed between the laser light source 21 and the variable light attenuator 41, which is upstream of the variable light attenuator 41, and thus laser light before being attenuated by the variable light attenuator 41 is distributed to the reference cell 26. Accordingly, the reference cell 26 is analyzed by laser light having an appropriate emission intensity, and thus the analysis target gas is analyzed by laser light adjusted to an emission intensity suited for the concentration of soot and dust contained in the analysis target gas. Accordingly, the reference cell 26 can be analyzed with laser light having a suitable emission intensity which is higher than the emission intensity of laser light adjusted to an emission intensity suitable for the concentration of soot and dust.

As depicted in FIG. 2, in some embodiments, further provided are an insertion measurement probe 6 to be inserted into a measuring target site (which exists outside the vessel 2 of the gas analysis system 1B) where the analysis target gas exists, a first optical fiber 61 inserted through the insertion measurement probe 6 to guide laser light to the measurement target site from the variable light attenuator 41 in the vessel 2, and a second optical fiber 62, inserted through the insertion measurement probe 6, to guide the laser light from the measurement target site to the photodetector 22 inside the vessel 2.

With the above configuration, the insertion measurement probe 6 can be inserted into the measurement target site where the analysis target gas exists. Accordingly, it is possible to analyze the analysis target gas which exists in the target measurement site into which the insertion measurement probe can be easily inserted.

As depicted in FIG. 2, in some embodiments, the insertion measurement probe 6 includes a measurement part 63 disposed in a light path between an output surface of the first optical fiber 61 from which the laser light is emitted and an input surface of the second optical fiber 62 into which the laser light enters. The analysis target gas exists at the measurement part 63. An optical system may be disposed in the light path between the output surface of the first optical fiber 61 and the input surface of the second optical fiber 62, to guide laser light emitted from the output surface of the first optical fiber 61 to the input surface of the second optical fiber 62 via the measurement part 63.

With the above configuration, the analysis target gas exists in the measurement part 63 disposed in the light path between the output surface of the first optical fiber 61 from which the laser light is emitted and the input surface of the second optical fiber 62 into which the laser light enters, and thus it is possible to analyze the analysis target gas reliably. Further, it is possible to reduce the length of the light path, and thus it is possible to obtain data in a local range through which the laser light transmits, even when the concentration of soot and dust is high and the analysis target gas cannot be analyzed as a whole.

Figure 5:
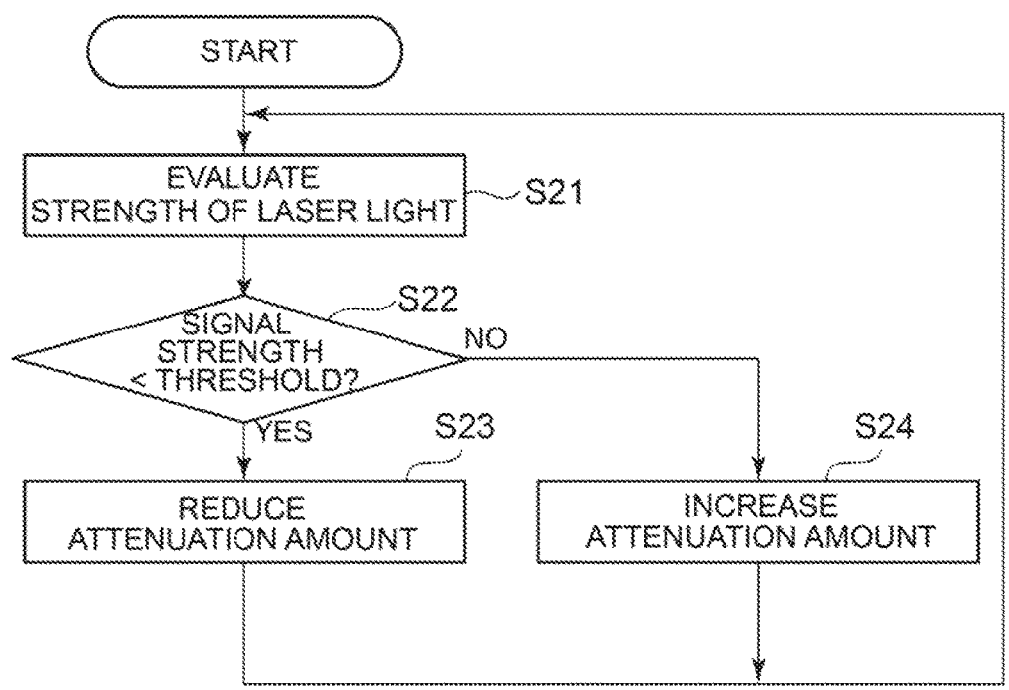
FIG. 5 is a flowchart showing a control of the attenuation-amount controller depicted in FIGS. 1 and 2.

FIG. 5 is a flowchart showing a control of the attenuation amount controller 43 depicted in FIGS. 1 and 2.

As shown in FIG. 5, in some embodiments, the attenuation amount controller 43 performs a control so as to increase the attenuation amount (step S24) if the intensity of laser light evaluated by the transmitted-light amount detector 42 is greater than a threshold (step S22: NO), or reduce the attenuation amount (step S23) if the intensity of laser light does not exceed the threshold (step S22: NO).

With this configuration, the attenuation amount is increased if the intensity of laser light evaluated by the transmitted-light amount detector 42 is greater than a threshold, and the attenuation amount is reduced if the intensity of the laser light is not greater than the threshold, which makes it possible to maintain the emission intensity of laser light having transmitted through the analysis target gas appropriately. Accordingly, it is possible to analyze the analysis target gas even when the concentration of soot and dust contained in the analysis target gas is high, and also it is possible to analyze the analysis target gas accurately even when the concentration of soot and dust contained in the analysis target gas becomes low.

In some embodiments, the threshold is set to a value not less than 80% of the maximum output value of the photodetector 22.

With this configuration, the threshold is set to a value not less than 80% of the maximum output value of the photodetector 22, and thus the attenuation amount is reduced if the intensity of laser light is less than 80% of the maximum output value of the photodetector 22. Accordingly, light of at least 80% of the maximum output value enters the photodetector 22, and thus it is possible to maintain a high detection accuracy.

FIG. 6 is a conceptual diagram of a boiler 7 provided with a gas analysis system according to an embodiment.

As shown in FIG. 6, in some embodiments, the boiler 7 includes a furnace 700 and at least one burner 710 for combusting fuel in the furnace 700. The boiler 7 may be a powdered-coal boiler configured to be capable of combusting powdered coal.

The boiler 7 includes a gas analysis system 1 having the above configuration, whereby it is possible to analyze combustion gas inside the furnace 700 with the gas analysis system 1. Thus, the laser light source 21 of the gas analysis system 1 is disposed so that laser light transmits through combustion gas, which is the analysis target gas, at an observation point P disposed in the furnace 700 of the boiler 7.

In some embodiments, the gas analysis system 1 is configured to analyze combustion gas inside the furnace 700 at the downstream side of the burner 710. Specifically, the observation point P is disposed on the downstream side of the burner 710 inside the furnace 700, and the laser light source 21 is disposed so that laser light transmits through the observation point P.

As described above, with the gas analysis system 1 analyzing combustion gas in the furnace 500 at the downstream side of the burner 710, it is possible to analyze combustion gas with high accuracy even if the concentration of soot and dust (e.g. concentration of soot and dust coming from powdered-coal fuel) changes considerably in response to a change in the operational condition of the boiler 7 (e.g. a change in the type of fuel, increase or decrease in the efficiency).

In an embodiment, the boiler 7 further includes an additional air supplying part 720 for supplying additional combustion air into the furnace 700 at the downstream side of the burner 710. Further, the gas analysis system 1 is configured to analyze combustion gas inside the furnace 700, at the downstream side of the burner 710 and at the upstream side of the additional air supplying part 720. Specifically, the laser light source 21 is disposed so that laser light passes through the observation point P on the downstream side of the burner 710 and the upstream side of the additional air supplying part 720 inside the furnace 700.

With the boiler 7 having the above configuration, a reduction combustion region 730 is formed on the downstream side of the burner 710 and the upstream side of the additional air supplying part 720. The composition of combustion gas in the reduction combustion region 730 is an important piece of information for appropriate operation control for the boiler 7. However, the concentration of soot and dust in the reduction combustion region 730 is high, and thus it is not easy to analyze combustion gas in the reduction combustion region 730.

In this regard, the gas analysis system 1 of the above configuration includes the attenuation amount controller 43 for controlling the attenuation amount of the variable light attenuator 41 on the basis of the transmitted light amount of laser light evaluated by the transmitted-light amount detector 42, and thus it is possible to analyze combustion gas with high accuracy in the reduction combustion region 730 having a high concentration of soot and dust. Thus, it is possible to perform an appropriate operation control on the boiler 7 by utilizing an accurate analysis result of combustion gas in the reduction combustion region 730.

In the embodiment depicted in FIG. 6, laser light is input into the boiler 7 to measure the concentration of oxygen and the concentration of soot and dust in combustion exhaust gas directly, to verify whether it is possible to perform contact-free measurement directly without sampling the concentration of gas and the concentration of solid particles in the combustion furnace and the flue portion.

In the embodiment depicted in FIG. 6, two measurement windows 753, 754 are disposed on a side wall of the furnace 700 of the boiler 7. The measurement windows 753, 754 are disposed below the additional air supplying part 720, at a position where laser light can be directly projected into the furnace 700. The laser light source 21 is disposed so as to face the measurement window 753. The light-receiving part 22 is disposed so as to face the measurement window 754.

The laser light source 21 is configured to receive the modulation signals S2, S3 outputted from the modulation part 31 inside a boiler control chamber 8. Further, the light-receiving part 22 outputs the light receiving signal to the analysis part 38 of the boiler control chamber. Further, the modulation part 31 outputs the modulation signals S2, S3 to the analysis part 38.

With the above configuration, laser light emitted from the laser light source 21 transmits through combustion gas, which is an analysis target gas, at the observation point P disposed inside the furnace 700 inside the boiler 7, and thereby it is possible to analyze combustion gas disposed at the observation point P disposed inside the furnace 700 of the boiler 7.

As depicted in FIG. 6, in some embodiments, the observation point P is disposed between the reduction combustion region 730 and a combustion completion region 740.

With the above configuration, laser light emitted from the laser light source 21 transmits through combustion gas, which is the analysis target gas, at the observation point P disposed between the reduction combustion region 730 and the combustion completion region 740, it is possible to analyze combustion gas disposed between the reduction combustion region 730 and the combustion completion region 740.

In some embodiments, the gas analysis apparatus 3 analyzes the oxygen concentration, the carbon monoxide concentration, and the gas temperature of combustion gas, which is the analysis target gas, at the observation point P.

With the above configuration, the gas analysis apparatus 3 analyzes the oxygen concentration, the carbon monoxide concentration, and the gas temperature of combustion gas, which is an analysis target gas, at the observation point P, and thereby it is possible to determine the operational state of the boiler 7.

Further, excessive oxygen is reduced by controlling primary air, secondary air, and fuel supply amount on the basis of the measurement results of the oxygen concentration and the carbon monoxide concentration, and thereby it is possible to improve the generator power generation efficiency and to reduce NOx.

For instance, an increase or decrease value is determined for primary air, secondary air, the fuel supply amount, or the supply ratio of primary air to secondary air, to achieve the optimum combustion region, on the basis of the concentration distribution of oxygen and carbon monoxide, and the temperature distribution, in the reduction combustion region, and is transmitted to the boiler control part (not depicted). The optimum combustion region refers to a region where the combustion state is such that NOx decreases and the combustion efficiency improves.

Embodiments of the present invention were described in detail above, but the present invention is not limited thereto, and various amendments and modifications may be implemented.

For instance, even when the concentration of soot and dust is high at the observation point P of the boiler 7 and the entire combustion gas cannot be analyzed, it is possible to obtain data in a local range by inserting the insertion measurement probe 6 with a reduced light path, and thereby it is possible to analyze the oxygen concentration, the carbon monoxide concentration, and the gas temperature of combustion gas.

DESCRIPTION OF REFERENCE NUMERAL 1 (1A, 1B) Gas analysis system
2 Vessel
21 Laser light source
22 Photodetector (standard photo detector)
25 Light distributor
26 Reference cell
261, 262 Window
27 Photodetector
3 Gas analysis apparatus
31 Modulation part
311 First function generator (modulation component generator)
315 Second function generator (wavelength sweep function generator)
32 Phase sensitive detector
33 DC component detector
34 Personal Computer
35 Phase sensitive detector
36 DC component detector
37 Light source driver
38 Analysis part
41 Variable light attenuator
42 Transmitted-light amount detector
43 Attenuation amount controller
5 Measurement cell
51, 52 Gas pipe
53 Input window
54 Output window
6 Insertion measurement probe
61 First optical fiber
62 Second optical fiber
63 Measurement part
7 Boiler
700 Furnace
710 Burner
730 Reduction combustion region
740 Combustion completion region
753 Measurement window
754 Measurement window
8 Boiler control chamber

The invention claimed is:

1. A gas analysis system, comprising:
a laser light source for emitting a laser light to be transmitted through an analysis target gas;
a photodetector configured to receive the laser light transmitted through the analysis target gas, for outputting a signal corresponding to an emission intensity of the received laser light;
a gas analysis apparatus for analyzing the analysis target gas on the basis of the signal outputted from the photodetector;
a variable light attenuator disposed between the analysis target gas and the laser light source;
a transmitted-light amount detector configured to evaluate a transmitted light amount of the laser light transmitted through the analysis target gas on the basis of the signal outputted from the photodetector;
an attenuation amount controller configured to control an attenuation amount of the variable light attenuator on the basis of the transmitted light amount of the laser light evaluated by the transmitted-light amount detector;
a vessel housing the laser light source, the photodetector, and the variable light attenuator, the vessel being filled with an inert gas; and an insertion measurement probe which is configured to be insertable into a measurement target site disposed outside the vessel, the insertion measurement probe including:
- a first optical fiber extending from the variable light attenuator inside the vessel to the measurement target site outside the vessel;
- a second optical fiber extending from the photodetector inside the vessel to the measurement target site outside the vessel; and
- an optical system disposed between an output surface of the first optical fiber and an input surface of the second optical fiber.

2. The gas analysis system according to claim 1,
wherein the photodetector is configured to output an output voltage in proportion to the emission intensity of the received laser light as the signal, and
wherein the transmitted-light amount detector is configured to evaluate the transmitted light amount of the laser light transmitted through the analysis target gas on the basis of the output voltage outputted from the photodetector.

3. The gas analysis system according to claim 1, wherein the attenuation amount controller is configured to increase the attenuation amount if an intensity of the laser light evaluated by the transmitted-light amount detector is greater than a threshold, and to reduce the attenuation amount if the intensity of the laser light is not greater than the threshold.

4. The gas analysis system according to claim 3, wherein the threshold is set to a value which is at least 80% of a maximum output value of the photodetector.

5. The gas analysis system according to claim 1, wherein the laser light source is disposed so that the laser light transmits through a combustion gas which serves as the analysis target gas, at an observation point disposed inside a furnace of a boiler.

6. The gas analysis system according to claim 5, wherein the observation point is disposed between a burner of the boiler and an additional air supplying part, inside the furnace.

7. The gas analysis system according to claim 1, wherein the gas analysis apparatus is configured to analyze an oxygen concentration, a carbon monoxide concentration, and a gas temperature of the combustion gas serving as the analysis target gas, at the observation point.

8. The gas analysis system according to claim 1, further comprising:
- a light distributor, disposed between the laser light source and the variable light attenuator, for distributing a part of the laser light emitted from the laser light source;
- a reference cell which contains a predetermined amount of the analysis target gas and through which the part of the laser light distributed by the light distributor transmits; and
- a standard photo detector configured to receive the part of the laser light transmitted through the reference cell, for outputting a standard signal corresponding to an emission intensity of the part of the received laser light,
wherein the gas analysis apparatus is configured to calibrate an analysis result of the analysis target gas on the basis of the standard signal outputted by the standard photo detector.

9. The gas analysis system according to claim 1, configured to maintain an output amount of the laser source and a gain of the photodetector constant during gas analysis.

10. The gas analysis system according to claim 1,
wherein the insertion measurement probe has a measurement part disposed in a light path between the output surface of the first optical fiber from which the laser light is emitted and the input surface of the second optical fiber into which the laser light enters, and
wherein the analysis target gas exists at the measurement part.

11. The gas analysis system according to claim 1, further comprising a low-pass filter for removing a noise component, disposed between the photo detector and the transmitted-light amount detector.

12. A boiler, comprising:
a furnace;
a burner for combusting fuel in the furnace; and
the gas analysis system according to claim 1, configured to analyze a combustion gas in the furnace at a downstream side of the burner.

13. The boiler according to claim 12, further comprising an additional air supplying part for supplying an additional combustion air into the furnace, at the downstream side of the burner,
wherein the gas analysis system is configured to analyze the combustion gas at a position downstream of the burner and upstream of the additional air supplying part, inside the furnace.

* * * * *